US009163226B2

(12) United States Patent
Wieland et al.

(10) Patent No.: US 9,163,226 B2
(45) Date of Patent: Oct. 20, 2015

(54) STORAGE-STABLE LIQUID WASHING OR CLEANING AGENT CONTAINING PROTEASES

(75) Inventors: Susanne Wieland, Zons/Dormagen (DE); Petra Siegert, Haan (DE); Astrid Spitz, Moers (DE); Karl-Heinz Maurer, Erkrath (DE); Timothy O'Connell, Duesseldorf (DE); Inken Prueser, Duesseldorf (DE); Marc-Steffen Schiedel, Duesseldorf (DE); Thomas Eiting, Duesseldorf (DE); Dorota Sendor-Mueller, Duesseldorf (DE); Thorsten Bastigkeit, Wuppertal (DE); Konstantin Benda, Duesseldorf (DE); Sven Mueller, Duisberg (DE)

(73) Assignee: BASF SE, Ludwigshafen (DE)

( * ) Notice: Subject to any disclaimer, the term of this patent is extended or adjusted under 35 U.S.C. 154(b) by 43 days.

(21) Appl. No.: 13/422,260

(22) Filed: Mar. 16, 2012

(65) Prior Publication Data

US 2012/0238005 A1 Sep. 20, 2012

Related U.S. Application Data

(63) Continuation of application No. PCT/EP2010/063556, filed on Sep. 15, 2010.

(30) Foreign Application Priority Data

Sep. 16, 2009 (DE) .......................... 10 2009 029 513

(51) Int. Cl.

| | | |
|---|---|---|
| *C12Q 1/37* | (2006.01) | |
| *C12N 9/50* | (2006.01) | |
| *D06M 16/00* | (2006.01) | |
| *C11D 3/00* | (2006.01) | |
| *C11D 9/50* | (2006.01) | |
| *C07H 21/04* | (2006.01) | |
| *C12N 9/54* | (2006.01) | |
| *C11D 3/36* | (2006.01) | |
| *C11D 7/36* | (2006.01) | |
| *C11D 3/386* | (2006.01) | |

(52) U.S. Cl.
CPC *C12N 9/54* (2013.01); *C11D 3/361* (2013.01); *C11D 3/38618* (2013.01); *C11D 7/36* (2013.01)

(58) Field of Classification Search
None
See application file for complete search history.

(56) References Cited

U.S. PATENT DOCUMENTS

| | | | |
|---|---|---|---|
| 6,228,827 B1 | 5/2001 | Penninger et al. | |
| 6,417,151 B1 | 7/2002 | Grothus et al. | |
| 7,300,782 B2 | 11/2007 | Breves et al. | |
| 7,510,859 B2 | 3/2009 | Wieland et al. | |
| 2004/0259222 A1 | 12/2004 | Breves et al. | |
| 2005/0026269 A1 | 2/2005 | Kottwitz et al. | |
| 2007/0128129 A1 | 6/2007 | Stehr et al. | |
| 2009/0170745 A1 | 7/2009 | Merkel et al. | |
| 2009/0275493 A1 | 11/2009 | Siegert et al. | |

FOREIGN PATENT DOCUMENTS

| | | |
|---|---|---|
| WO | 9221760 A1 | 12/1992 |
| WO | 9523221 A1 | 8/1995 |
| WO | 03057713 A2 | 7/2003 |
| WO | 2005056782 A2 | 6/2005 |
| WO | 2005118793 A2 | 12/2005 |

OTHER PUBLICATIONS

Altschul, Stephen F. et al. "Basic Local Alignment Search Tool." J. Mol. Biol., vol. 215, 1990, pp. 403-410.
Altschul, Stephen F. et al. "Gapped BLAST and PSI-BLAST: a new generation of protein database search programs." Nucleic Acids Research, vol. 25, No. 17, 1997, pp. 3389-3402.
Chenna, Ramu et al. "Multiple sequence alignment with the Clustal series of programs." Nucleic Acids Research, vol. 31, No. 13, 2003, pp. 3497-3500.
Notredame, Cedric, et al. "T-Coffee: A Novel Method for Fast and Accurate Multiple Sequence Alignment." J. Mol. Biol., vol. 302, 2000, pp. 205-217.
Tenside [Surfactants] (1970) vol. 7, pp. 125-132.
Gornall, Allan G., et al. "Determination of Serum Proteins by Means of the Biuret Reaction." J. Biol. Chem., vol. 177, 1948, pp. 751-766.
DelMar, E.G., et al. "A Sensitive new Substrate for Chymotrysin." Analytical Biochemistry, vol. 99, 1979, pp. 316-320.
International Cosmetic Ingredient Dictionary & Handbook.The Cosmetic Toiletry and Fragrance Association, 7th Edition, 1997.
Fritsch et al. "Molecular cloning: a laboratory manual," Cold Spring Harbour Laboratory Press, 1989.

*Primary Examiner* — Iqbal H Chowdhury
(74) *Attorney, Agent, or Firm* — Marshall, Gerstein & Borun LLP

(57) ABSTRACT

Phosphonate-containing liquid washing or cleaning agent exhibiting advantageous proteolytic activity and improved storage stability comprising a protease having an amino acid sequence which is at least 80% identical to the amino acid sequence stated in SEQ ID NO. 1 and which comprises in position 99 in the numbering according to SEQ ID NO. 1 the amino acid glutamic acid (E) or aspartic acid (D) or the amino acid asparagine (N) or glutamine (Q) or the amino acid alanine (A) or glycine (G) or serine (S).

14 Claims, No Drawings

STORAGE-STABLE LIQUID WASHING OR CLEANING AGENT CONTAINING PROTEASES

CROSS REFERENCE TO RELATED APPLICATIONS

The present application is a continuation of International Patent Application No. PCT/EP2010/063556 filed 15 Sep. 2010, which claims priority to German Patent Application No. 10 2009 029 513.5 filed 16 Sep. 2009, both of which are incorporated herein by reference.

The invention relates to the field of liquid washing and cleaning agents. In particularly, the invention relates to liquid enzyme-containing washing and cleaning agents having defined proteases in combination with a phosphonate, and additionally proposes uses and methods wherein such agents are used. The invention furthermore relates to uses of defined proteases in liquid washing or cleaning agents having a phosphonate.

Use of subtilisin proteases has been preferred for washing and cleaning agents. Proteases used in washing or cleaning agents and known in the art either originally originate from microorganisms, for instance, of the genera *Bacillus, Streptomyces, Humicola,* or *Pseudomonas*, and/or are produced by suitable microorganisms using per se known biotechnological methods such as by transgenic expression hosts from the genera *Bacillus* or filamentous fungi.

Phosphonates are found in both modern liquid washing agents and cleaning agents. They are used, for example, as complexing agents, for preventing precipitation or as bleaching agent stabilizers. When present as complexing agents, they serve for example to soften water. They are capable of enveloping cations such as $Ca^{2+}$ in the solution, thus modifying the chemical behavior of the cation. With calcium, the property of forming water hardness disappears. Other cations may also be complexed and thus protected from chemical reactions. They can also serve as corrosion inhibitors or as stabilizers for peroxides, particularly in bleaching agents.

International Patent Application WO 95/23221 discloses proteases or protease variants of the subtilisin type from *Bacillus lentus* DSM 5483, which are suitable for use in washing or cleaning agents. These proteases also include one which may have an amino acid substitution R99E, A, S or G. It additionally teaches that the washing agents may contain a phosphonate, in particular a polyphosphonate. The washing agents can be solid or liquid. However, this document does not disclose any specific washing and/or cleaning agent containing a phosphonate in combination with such a protease.

One disadvantage of prior art protease-containing liquid washing and cleaning agents is that they often do not exhibit satisfactory proteolytic activity, particularly not at low temperatures, for example, from 10° C. to 50° C., particularly 10° C. to 40° C. or 20° C. to 40° C. The washing or cleaning agents therefore do not exhibit optimum cleaning performance. A further disadvantage of prior art protease-containing liquid washing and cleaning agents is that they have inadequate storage stability and therefore lose a considerable degree of proteolytic activity after only a short time.

The present invention attempts to overcome the stated disadvantages by providing liquid washing or cleaning agents having advantageous proteolytic activity, particularly at temperatures such as those stated above, and also exhibit improved storage stability.

The present invention accordingly provides a liquid washing or cleaning agent comprising—
(a1) a protease having an amino acid sequence which is at least 80% identical to the amino acid sequence stated in SEQ ID NO. 1 and comprises in position 99 in the numbering according to SEQ ID NO. 1 the amino acid glutamic acid (E) or aspartic acid (D), or
(a2) a protease having an amino acid sequence which is at least 80% identical to the amino acid sequence stated in SEQ ID NO. 1 and comprises in position 99 in the numbering according to SEQ ID NO. 1 the amino acid asparagine (N) or glutamine (Q), or
(a3) a protease having an amino acid sequence which is at least 80% identical to the amino acid sequence stated in SEQ ID NO. 1 and comprises in position 99 in the numbering according to SEQ ID NO. 1 the amino acid alanine (A) or glycine (G) or serine (S); and
(b) a phosphonate.

It was surprisingly noted that a liquid washing or cleaning agent having the combination of such a protease with a phosphonate exhibits advantageous cleaning performance with respect to protease-sensitive soiling and is also advantageously stable in storage. Preferred embodiments of agents according to the invention exhibit advantageous cleaning performance in terms of at least one protease-sensitive type of soiling at temperatures of from 10° C. to 60° C., preferably also at low temperatures, for example, from 10° C. to 50° C., 10° C. to 40° C., or 20° C. to 40° C. An agent according to the invention therefore provides improved removal of at least one, preferably a plurality of protease-sensitive types of soiling on textiles and/or hard surfaces such as dishes. Regarding the above-mentioned International Patent Application WO 95/23221, the present invention therefore relates to a particularly advantageous selection which results in a high performance, storage-stable liquid washing agent or liquid cleaning agent.

For the purposes of the invention, cleaning performance refers to lightening performance with regard to one or more types of soiling, particularly laundry soiling or crockery soiling, which are sensitive to degradation by the protease. Examples of such laundry soiling are blood-milk/ink on cotton, whole egg/pigment on cotton, chocolate-milk/ink on cotton, peanut oil-pigment/ink on polyester/cotton, grass on cotton or cocoa on cotton, in particular as stated further below. Examples of such crockery soiling are milk, minced meat or egg yolk. For the purposes of the invention, both the washing and cleaning agent which comprises the protease or the washing and cleaning liquor formed by this agent and the protease itself exhibit a respective cleaning performance. Cleaning performance of the hydrolytic enzyme thus contributes to the cleaning performance of the agent or washing or cleaning liquor formed by the agent. Cleaning performance is preferably determined as stated further below.

Washing or cleaning liquor is understood to be the working solution containing the washing or cleaning agent. This solution acts on textiles or fabric (washing liquor) or hard surfaces (cleaning liquor) and thus comes into contact with the soiling present on textiles or fabrics or hard surfaces. The washing or cleaning liquor conventionally arises when the washing or cleaning process begins and the washing or cleaning agent is diluted with water, for example, in a washing machine, dishwashing machine or in another suitable container.

The washing or cleaning agent present in a washing or cleaning liquor according to the invention comprises an amino acid sequence which is at least 80% identical to the amino acid sequence stated in SEQ ID NO. 1 and which comprises in position 99 in the numbering according to SEQ ID NO. 1 the amino acid glutamic acid (E) or aspartic acid (D) or the amino acid asparagine (N) or glutamine (Q) or the amino acid alanine (A) or glycine (G) or serine (S). More preferably, the amino acid sequence is at least 81%, 82%, 83%, 84%, 85%, 86%, 87%, 88%, 89%, 90%, 91%, 92%, 93%, 94%, 95%, 96%, 97%, 98% and very particularly preferably 99% identical to the amino acid sequence stated in SEQ ID NO. 1. SEQ ID NO. 1 is the sequence of the mature alkaline protease from *Bacillus lentus* DSM 5483, disclosed in International Patent Application WO 92/21760.

It has now been found that the addition of such a protease to a liquid washing or cleaning agent containing a phosphonate results in a particularly storage-stable liquid washing agent, particularly with regard to its residual proteolytic activity after storage, particularly after storage of 1 to 5 weeks, 1 to 4 weeks, 1.5 to 3 weeks and particularly preferably after 2 weeks.

A protease present in a washing or cleaning agent according to the invention exhibits proteolytic activity, that is, it can hydrolyze peptide bonds of a polypeptide or protein. It is therefore an enzyme which catalyzes the hydrolysis of peptide bonds and is thus capable of cleaving peptides or proteins, particularly a subtilisin.

In a further embodiment, the protease in the washing or cleaning agent further contains at least one of the following amino acids in the numbering according to SEQ ID NO. 1:
(a) threonine in position 3 (3T),
(b) isoleucine in position 4 (4I),
(c) alanine, threonine or arginine in position 61 (61A, 61T or 61R),
(d) aspartic acid or glutamic acid in position 154 (154D or 154E),
(e) proline in position 188 (188P),
(f) methionine in position 193 (193M),
(g) isoleucine in position 199 (199I),
(h) aspartic acid, glutamic acid or glycine in position 211 (211D, 211E or 211G),
(i) combinations of amino acids (a) to (h).

In addition to one of the stated amino acids in position 99, the protease therefore has one or more of the above-stated amino acids in the respective positions. These amino acids may bring about further advantageous properties and/or further enhance existing properties. In particular, these amino acids can bring about an increase in proteolytic activity and/or stability of the protease in a liquid washing or cleaning agent or in the washing liquor formed by this washing or cleaning agent. By addition of such a protease to a liquid washing or cleaning agent containing a phosphonate, a particularly storage-stable liquid washing agent is obtained, particularly with regard to its residual proteolytic activity after storage, particularly after a storage period of 1 to 5 weeks, 1 to 4 weeks, 1.5 to 3 weeks and particularly preferably after 2 weeks.

Amino acid positions are defined here by an alignment of the amino acid sequence of the protease to be used with the amino acid sequence of the protease from *Bacillus lentus*, as stated in SEQ ID NO. 1. Since the protease from *Bacillus lentus* in the prior art is an important reference molecule for describing proteases and amino acid changes, it is advantageous to refer to the numbering of the protease from *Bacillus lentus* (SEQ ID NO. 1) in amino acid position assignment. The numbering is also based on the mature protein. This assignment should also be used if the amino acid sequence of the protease used has a larger number of amino acid residues than the protease from *Bacillus lentus* according to SEQ ID NO. 1. Based on the stated positions in the amino acid sequence of the protease from *Bacillus lentus*, the amino acid positions in a protease used according to the invention are those which are assigned to precisely these positions in an alignment.

Apart from position 99, particularly advantageous positions include positions 3, 4, 61, 154, 188, 193, 199 and 211, to be assigned in an alignment with SEQ ID NO. 1 and thus in the numbering according to SEQ ID NO. 1. The following amino acid residues are in the stated positions in the wild-type molecule of the protease from *Bacillus lentus*: S3, V4, G61, S154, A188, V193, V199, and L211. Amino acids 3T, 4I, 61A, 154D, 154E, 211D, 211G and 211E are particularly preferred, provided that the corresponding positions in a protease to be used according to the invention have not already been adopted naturally by one of these preferred amino acids. The 3T and 4I substitutions lead, for example, via a stabilizing effect on the molecule to an improvement in storage stability and cleaning performance of the protease, and thus to improved cleaning performance of a phosphonate-containing liquid washing or cleaning agent containing the protease.

Due to the above-stated amino acids provided for the respective position, further sequence deviations from SEQ ID NO. 1 may arise, if SEQ ID NO. 1 comprises another amino acid in the respective position. Depending on the number of sequence deviations from SEQ ID NO. 1 which are present, different maximum identity values therefore arise which a protease to be used according to the invention in SEQ ID NO. 1 may exhibit, even should it match SEQ ID NO. 1 with regard to all other amino acids. This factor should be taken into account for every possible combination of the proposed amino acids in each individual case and is furthermore also dependent on the length of the amino acid sequence of the protease. For example, with one, two, three, four, five, six, seven, eight or nine sequence changes, maximum identity amounts to 99.63%, 99.26%, 98.88%, 98.51%, 98.14%, 97.77%, 97.40%, 97.03% or 96.65% respectively for an amino acid sequence 269 amino acids in length, or to 99.64%, 99.27%, 98.91%, 98.55%, 98.18%, 97.82%, 97.45%, 97.09% or 96.73% respectively for an amino acid sequence 275 amino acids in length.

The identity of nucleic acid or amino acid sequences is determined by sequence comparison. Such a comparison proceeds by assigning similar sequences to one another in the nucleotide sequences or amino acid sequences. This sequence comparison is preferably performed based on conventionally used BLAST algorithm established in the prior art (e.g., Altschul, S. F., Gish, W., Miller, W., Myers, E. W. & Lipman, D. J., "Basic local alignment search tool." J. Mol. Biol. 215, (1990) pp. 403-410, and Altschul, Stephan F., Thomas L. Madden, Alejandro A. Schaffer, Jinghui Zhang, Hheng Zhang, Webb Miller, and David J. Lipman, "Gapped BLAST and PSI-BLAST: a new generation of protein database search programs"; Nucleic Acids Res., 25, (1997) pp. 3389-3402), and generally proceeds by assigning similar sequences of nucleotides or amino acids in the nucleic acid or amino acid sequences to one another. A tabular assignment of the positions in question is known as an alignment. A further algorithm available in the prior art is the FASTA algorithm. Sequence comparisons (alignments), particularly multiple sequence comparisons, are conventionally created using computer software. Use is often made, for example, of the Clustal series (cf., for example, Chenna et al., "Multiple sequence alignment with the Clustal series of programs", Nucleic Acid Research 31, (2003) pp. 3497-3500), T-Coffee (cf., for example, Notredame at al., "T-Coffee: A novel method for multiple sequence alignment", J. Mol. Biol. 302, (2000) pp. 205-217) or programs which are based on these programs or algorithms. Use is often made, for example, of Clustal (cf. for example Chenna et al., "Multiple sequence alignment with the Clustal series of programs", Nucleic Acid Research 31, (2003) 3497-3500), T-Coffee (cf. for example Notredame et al., "T-Coffee: A novel method for multiple sequence alignment", J. Mol. Biol. 302, (2000) pp. 205-217) and of BLAST or FASTA for database searches, or programs based on these programs or algorithms. For the purposes of the present invention, sequence comparisons and alignments are preferably performed with the computer program Vector NTI® Suite 10.3 (Invitrogen Corporation, 1600 Faraday Avenue, Carlsbad, Calif., USA) using the preset default parameters.

Such a comparison allows a statement to be made about the similarity of the compared sequences. It is conventionally stated in percent identity (i.e., the proportion of identical nucleotides or amino acid residues therein or in an alignment of mutually corresponding positions). The broader term "homology" also includes consideration of amino acid substitutions conserved in amino acid sequences, thus amino acids with similar chemical activity, since they generally exercise similar chemical activities within the proteins. The similarity of the compared sequences may therefore also be stated in percent homology or percent similarity. Statements regarding identity and/or homology may be made over entire polypeptides or genes or only over individual domains. Homologous or identical domains of various nucleic acid or amino acid sequences are therefore defined by matches in the sequences. Such domains often exhibit identical functions. They may be small and comprise only a few nucleotides or amino acids. Often such small domains exercise functions which are essential for the overall activity of the protein. It may therefore be meaningful to relate sequence matches to only individual, optionally small domains. If not stated otherwise, however, statements regarding identity or homology in the present application relate to the entire length of the nucleic acid or amino acid sequence indicated in each case.

In a further embodiment, the protease comprises an amino acid sequence which, as indicated above, is identical to the amino acid sequence stated in SEQ ID NO. 1 and which is obtained or is obtainable from a protease according to SEQ ID NO. 1 by conservative amino acid mono- or polysubstitution. The term "conservative amino acid substitution" means the substitution (exchange) of one amino acid residues for another amino acid residue, this substitution not leading to a change in polarity or charge in the position of the substituted amino acid (e.g., the substitution of a nonpolar amino acid residue for another nonpolar amino acid residue). Conservative amino acid substitution for the purposes of the invention comprise for example: G=A=S, I=V=L=M, D=E, N=Q, K=R, Y=F, S=T, G=A=I=V=L=M=Y=F=W=P=S=T.

In a further embodiment, a washing or cleaning agent according to the invention is further characterized in that its cleaning performance corresponds at least to that of a washing or cleaning agent containing a protease having an amino acid sequence corresponding to the amino acid sequence stated in SEQ ID NO. 2, SEQ ID NO. 3, SEQ ID NO. 4, SEQ ID NO. 5, SEQ ID NO. 6, SEQ ID NO. 7 or SEQ ID NO. 8. Cleaning performance is determined in a washing system containing a washing agent at a rate of addition of from 4.0 to 8.0 grams per liter of washing liquor and the protease, the proteases to be compared being used at identical activity, and cleaning performance being determined relative to one or more of the soiling types blood-milk/ink on cotton, whole egg/pigment (whole egg/soot) on cotton, peanut oil-pigment/ink on polyester/cotton and grass on cotton, in particular, relative to one or more of the following soiling types:

- blood-milk/ink on cotton: product no. C-05 obtainable from CFT (Center For Testmaterials) B.V. Vlaardingen, Netherlands;
- whole egg/pigment (whole egg/soot) on cotton: product no. 10N obtainable from wfk Testgewebe GmbH; Brüggen-Bracht, Germany, or product C—S-37 obtainable from CFT (Centre For Testmaterials) B.V. Vlaardingen, Netherlands;
- peanut oil-pigment/ink on polyester/cotton: product no. PC-10 obtainable from CFT (Center For Testmaterials) B.V. Vlaardingen, Netherlands;
- grass on cotton: product no. 164 obtainable from Eidgenössische Material- and Prüfanstalt (EMPA) Testmaterialien AG, St. Gallen, Switzerland, by measuring the degree of whiteness of the washed textiles, the washing process proceeding for at least 30 minutes, optionally 60 minutes, at a temperature of 20° C. and the water exhibiting a hardness of between 15.5 and 16.5° dH (German hardness degrees).

The washing agent for the washing system is a liquid washing agent, preferably of the composition indicated in Table 1 (all values stated in weight percent):

TABLE 1

| Ingredient | wt. % |
| --- | --- |
| $C_{12-18}$ fatty alcohol with 7 EO | 6.40 |
| Lin. $C_{10-C13}$ alkylbenzene sulfonate (sodium salt) | 5.35 |
| $C_{12-18}$ fatty acid (sodium salt) | 2.00 |
| Citric acid (sodium salt) | 1.20 |
| Phosphonate (Dequest ® 2066) | 0.50 |
| Boric acid (Na salt) | 1.00 |
| Polyacrylate thickener | 0.15 |
| Glycerol | 3.00 |
| Ethanol | 1.00 |
| Silicone defoamer | 0.01 |
| Perfume | 0.70 |
| Dye, preservative | + |
| Water | Ad 100 |

The preferred rate of addition of this liquid washing agent amounts to 7.0 to 7.5 grams per liter of washing liquor, particularly 7.4 grams per liter of washing liquor. The weight of the liquid washing agent is determined in this respect, such that the details are related to the weight thereof. Washing is preferably performed in a pH value range of from pH 8 to pH 10.5, preferably pH 8 to pH 9.

The degree of whiteness (i.e., the lightening of the soiling) as a measure of cleaning performance is preferably determined using optical measurement methods, preferably photometrically. One instrument suitable for this purpose is, for example, the Minolta CM508d spectrophotometer. The instruments used for measurement are conventionally previously calibrated with a white standard, preferably the white standard supplied.

By using the respective protease at identical activity, it is ensured that the respective enzymatic properties (e.g., cleaning performance for specific types of soiling) are compared even in the event of possible divergence of the ratio of active substance to total protein (the values of the specific activity). As a general rule, low specific activity may be balanced by the addition of a larger amount of protein. Methods for determining protease activities are familiar to a person skilled in the art in the field of enzyme technology and are routinely used by such persons. For example, such methods are disclosed in Tenside [Surfactants], Vol. 7, (1970) pp. 125-132. Protease activity is preferably stated in protease units ("PU"). Suitable protease activities amount to, for example, 2.25, 5 or 10 PU per ml of washing liquor. Protease activity is not equal to zero, however.

Numerous proteases and particularly subtilisins are formed as "preproteins" (i.e., accompanied by a propeptide and a signal peptide). The function of the signal peptide conventionally consists in ensuring export of the protease from the cell producing it into the periplasm or the medium surrounding the cell, and the propeptide conventionally is necessary for correct folding of the protease. The signal peptide and propeptide are, as a rule, the N-terminal part of the preprotein. The signal peptide is cleaved under natural conditions from the rest of the protease by a signal peptidase. Correct, final, propeptide-assisted folding of the protease then takes place. The protease is then in its active form and itself cleaves off the propeptide. Once the propeptide has been cleaved off, the then mature protease, particularly subtilisin, exercises its catalytic activity without the originally present N-terminal amino acids. For industrial applications in general, and in particular for the purposes of the invention, mature proteases (i.e., enzymes processed after production thereof) are preferred over preproteins. The proteases may be further modified by the cells producing them after production of the polypeptide chain, for example, by linkage of sugar molecules, formylation, amination, etc. Such modifications are post-translational modifications and may, but not necessarily, exert an influence on the function of the protease.

In addition, the mature protease may also be truncated at its N-terminal and/or C-terminal end, such that a protease truncated relative to SEQ ID NO. 1, SEQ ID NO. 2, SEQ ID NO. 3, SEQ ID NO. 4, SEQ ID NO. 5, SEQ ID NO. 6, SEQ ID NO. 7 or SEQ ID NO. 8 (i.e., a fragment is present in the washing or cleaning agent according to the invention). All statements of identity relate here to that domain wherein the respective fragment is assigned in an alignment SEQ ID NO. 1. However, the respective fragment in each case includes that position assigned to position 99 in an alignment with SEQ ID NO. 1, and has a corresponding amino acid in this position. It advantageously also contains one or more of the positions described further above, and there comprises one or more corresponding amino acids. In addition, such a fragment is proteolytically active. A further preferred fragment in this respect comprises an amino acid sequence which matches SEQ ID NO. 1, SEQ ID NO. 2, SEQ ID NO. 3, SEQ ID NO. 4, SEQ ID NO. 5, SEQ ID NO. 6, SEQ ID NO. 7 or SEQ ID NO. 8 over a length of at least 50 or at least 60, 70, 80, 90, 100, 110, 120, 130, 140, 150, 160, 170, 180, 190, 200, 210, 220, 230, 240, 250, 260, 265, 266, 267 or 268 contiguous amino acid positions, taking account of the above-stated amino acids for position 99 and optionally also for positions 3 and/or 4 and/or 61 and/or 154 and/or 188 and/or 193 and/or 199 and/or 211. The cleaning performance of a liquid washing or cleaning agent according to the invention comprising such a fragment particularly preferably corresponds at least to that of a washing or cleaning agent containing a protease comprising an amino acid sequence, which corresponds to that amino acid sequence stated in SEQ ID NO. 2, SEQ ID NO. 3, SEQ ID NO. 4, SEQ ID NO. 5, SEQ ID NO. 6, SEQ ID NO. 7 or SEQ ID NO. 8, determined as stated above.

In addition, the protease present in an agent according to the invention may be adsorbed onto carrier substances and/or be embedded in encapsulating substances in order to protect them from premature inactivation. In the washing liquor (i.e., under conditions of use), the protease is then liberated and can exercise its proteolytic action.

The present invention also provides a liquid washing or cleaning agent comprising:

(a) a protease chosen from
  a. a protease comprising an amino acid sequence according to SEQ ID NO. 2, SEQ ID NO. 3, SEQ ID NO. 4, SEQ ID NO. 5, SEQ ID NO. 6, SEQ ID NO. 7, or SEQ ID NO. 8;
  b. a protease which, relative to SEQ ID NO. 2, SEQ ID NO. 3, SEQ ID NO. 4, SEQ ID NO. 5, SEQ ID NO. 6, SEQ ID NO. 7, or SEQ ID NO. 8, comprises an amino acid sequence modified in at least one position, the modification in the numbering according to SEQ ID NO. 1 being chosen from:
    i. threonine in position 3 (3T),
    ii. isoleucine in position 4 (4I),
    iii. alanine, threonine or arginine in position 61 (61A, 61T or 61R),
    iv. aspartic acid or glutamic acid in position 154 (154D or 154E),
    v. proline in position 188 (188P),
    vi. methionine in position 193 (193M),
    vii. isoleucine in position 199 (199I),
    viii. aspartic acid, glutamic acid or glycine in position 211 (211D, 211E or 211G),
    ix. combinations of amino acids (i) to (viii);
(b) a phosphonate.

These proteases are very particularly preferably used in a liquid washing or cleaning agent according to the invention. They are obtained on the basis of SEQ ID NO. 1 by substitution of the amino acid arginine in position 99 by the amino acid glutamic acid (E) or aspartic acid (D) or the amino acid asparagine (N) or glutamine (Q) or the amino acid alanine (A) or glycine (G) or serine (S) in the numbering according to SEQ ID NO. 1. These amino acid sequences are stated in the sequence listing as SEQ ID NO. 2, SEQ ID NO. 3, SEQ ID NO. 4, SEQ ID NO. 5, SEQ ID NO. 6, SEQ ID NO. 7 or SEQ ID NO. 8. Moreover, in addition to the amino acid provided for position 99, these proteases may comprise one or more of the above-described amino acids in positions 3, 4, 61, 154, 188, 193, 199 and 211, to be assigned in an alignment with SEQ ID NO. 1 and thus in the numbering according to SEQ ID NO. 1. In the case of these proteases too, the stated amino acids for these positions bring about further advantageous properties and/or further enhance existing properties. In particular, they bring about an increase in proteolytic activity and/or stability of the protease in a liquid washing or cleaning agent or in the washing liquor formed by this washing or cleaning agent. All the above explanations, insofar as applicable, apply accordingly to these particularly preferred proteases.

Phosphonates are salts and organic compounds, particularly esters of phosphonic acid. Primary (M'H$_2$PO$_3$ or HP(O)(OH)(OM')) and secondary (M'$_2$HPO$_3$ or HP(O)(OM')$_2$) phosphonates exist as salts, M' denoting a monovalent metal. These inorganic phosphonates are also known as primary or secondary phosphites. Inorganic phosphonates arise for example by reacting phosphonic acid HP(O)(OH)$_2$, in particular the stable tautomeric form of the phosphorous acid with one (primary) or two (secondary) equivalents of base, for example alkali metal hydroxide.

For the purposes of the present invention, organic P-substituted phosphonates having a phosphorus-carbon bond are preferred (organophosphorus compounds). Their general structure is R1P(O)(OR2)$_2$, with R1 and/or R2=alkyl, aryl or H, the alkyl or aryl residues comprising further substitutions or being capable of bearing further chemical groups. Organic P-substituted phosphonates arise, for example, as a result of the Michaelis-Arbusov reaction. Many of these phosphonates are soluble in water. Some industrially important phosphonates additionally bear amino group(s) of the type NR—$(CH_2)_x$-PO(OH)$_2$ (R=alkyl, aryl or H). Some of these aminophosphonates have structural similarities with complexing agents such as EDTA, NTA or DTPA and have a similar function.

Particularly preferred phosphonates include in particular organophosphonates such as 1-hydroxyethane-1,1-diphosphonic acid (HEDP), aminotri(methylenephosphonic acid) (ATMP, also known as amino-tris(methylenephosphonic acid) or nitrolotris(methylenephosphonic acid) (NTMP), diethylenetriaminepenta(methylenephosphonic acid) (DTPMP or DETPMP or DTPNT), ethylenediaminetetra(methylenephosphonic acid) (EDTMP, also known as ethylenediaminetetra(methylenephosphonic acid) and 2-phosphonobutane-1,2,4-tricarboxylic acid (PBS-AM, also known as 2-phosphonobutane-1,2,4-tricarboxylic acid or 3-carboxy-3-phosphonoadipic acid), which are mainly used in the form of the ammonium or alkali metal salts thereof. Particular preference is given to diethylenetriaminepenta(methylenephosphonic acid) sodium, particularly for washing agents according to the invention, and/or 1-hydroxyethane-1,1-diphosphonic acid (HEDP), in particular for dishwashing agents according to the invention, in particular automatic dishwashing agents. Such phosphonates are obtainable, for example, under the trade names Dequest® 2066 and Dequest® 2010 (in each case from Thermphos).

In a preferred embodiment, the phosphonate is present in an amount of 0.01 to 4 wt. %. Further preferred quantities of phosphonate present in the washing or cleaning agent are from 0.01 to 3 wt. %, from 0.01 to 2.5 wt. %, from 0.02 to 2.4 wt. %, from 0.02 to 2 wt. %, from 0.03 to 1.5 wt. % or from 0.05 to 1 wt. %.

The protease is present in a washing or cleaning agent according to the invention preferably in an amount of $1 \times 10^{-8}$ to 5 weight percent relative to active protein. The protease is increasingly preferably present in the agent in an amount of from 0.001 to 5 wt. %, more preferably 0.01 to 5 wt. %, still more preferably 0.05 to 4 wt. % and particularly preferably from 0.075 to 3.5 wt. %. Protein concentration can be determined by known methods, for example, the BCA method (bicinchoninic acid; 2,2'-biquinolyl-4,4'-dicarboxylic acid) or the biuret method (A. G. Gornau, C. S. Bardawill and M. M. David, J. Biol. Chem., 177, (1948) pp. 751-766).

In a further embodiment, the washing or cleaning agent further comprises a component chosen from—
(i) an anionic and/or polyanionic substance, and/or
(ii) a cationic and/or polycationic substance, and/or
(iii) a substance comprising hydroxyl and/or polyhydroxyl group(s).

It has been noted that the addition of such substances further improves the cleaning performance of washing and cleaning agents, particularly liquid washing or cleaning agents containing proteases, in particular those as described above, in particular at comparatively low temperatures, particularly from 10° C. to 50° C., 10° C. to 40° C., 10° C. to 30° C. and/or 20° C. to 40° C.

The substances indicated above under (i) are anionic or polyanionic substances (i.e., these substances bear at least one and preferably a number of negative charges). The substances are preferably a polymer with at least one negatively charged monomer, preferably with a plurality of negatively charged monomers. According to the invention this polymer is therefore preferably a negatively charged polymer. Preference is given, for example, to polymers of organic acids or the salts thereof, in particular polyacrylates and/or polysaccharide acids and/or polyacrylate copolymers and/or polysaccharide copolymers. In this respect, further preferred compounds are polyacrylic sulfonates or polycarboxylates and the salts thereof, copolymers or salts of the copolymers.

Examples of particularly preferred substances are Acusol 587D (polyacrylic sulfonate; Rohm & Haas/Dow Chemical), Acusol 445N (polycarboxylate sodium salt; Rohm & Haas/Dow Chemical), Acusol 590 (polyacrylate copolymer; Rohm & Haas/Dow Chemical), Acusol 916 (polyacrylate sodium salt; Rohm & Haas/Dow Chemical), Sokalan CP42 (modified polycarboxylate sodium salt; BASF), Sokalan PA 30CL (polycarboxylate sodium salt; BASF), Dequest P 9000 (polymaleic acid; Thermphos), alginic acid, poly-2-acrylamido-2-methyl-1-propanesulfonic acid, poly-4-styrene sulfonic acid-co-maleic acid sodium salt, polyacrylamido-co-acrylic acid sodium salt, polymethacrylic acid sodium salt, polymethyl vinyl ether-alt-maleic acid or polyvinyl sulfonic acid sodium salt.

The substances indicated above under (ii) are cationic or polycationic substances (i.e., these substances bear at least one and preferably a number of positive charges). The substances are preferably a polymer with at least one positively charged monomer, preferably with a plurality of positively charged monomers. According to the invention this polymer is therefore preferably a positively charged polymer. Examples of preferred compounds are salts of polyamines, polyethyleneimines or the copolymers thereof, salts of polyallylamines, salts of polydiallyl dimethyl ammonium compounds or polyacrylamide-co-diallyl dimethyl ammonium salt compounds).

The substances indicated under (iii) are substances having at least one hydroxyl and/or polyhydroxyl group, and preferably a plurality of hydroxyl and/or polyhydroxyl groups. In this respect, preference is given, for example, to polyvinyl alcohols such as those available under the trade name Mowiol (Kremer Pigmente GmbH & Co. KG).

It is expressly pointed out at this point that a specific substance may belong to one or more of above-stated groups (i) to (iii). For example, it may be an anionic polymer, which comprises one or more hydroxyl and/or polyhydroxyl group(s). Such a substance then belongs to groups (i) and (iii). A cationic polymer which comprises one or more hydroxyl and/or polyhydroxyl group(s) is likewise associated with groups (ii) and (iii).

It is likewise possible for the purposes of the present invention to use derivatives of the substances stated above as belonging to (i), (ii) or (iii). For the purposes of the present application, a derivative is understood to be a substance which is chemically modified on the basis of one of the above-stated substances, for example, by conversion of a side chain or by covalent bonding of another compound to the substance. Such a compound may, for example, be low molecular weight compounds such as lipids or mono-, oligo- or polysaccharides or amines or amine compounds. In addition, the substance may be glycosylated, hydrolyzed, oxidized, N-methylated, N-formylated or N-acetylated or contain methyl, formyl, ethyl, acetyl, t-butyl, anisyl, benzyl, trifluoroacetyl, N-hydroxysuccinimide, t-butyloxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulfenyl, 4-toluenesulfonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, or 2,2,5,7,8-pentamethylchromane-6-sulfonyl. A derivative is likewise understood to mean covalent or non-covalent bonding of the substance to a macromolecular substrate, or equally also non-covalent inclusion in suitable macromolecular cage structures. Coupling reactions with other macromolecular compounds, such as for instance polyethylene glycol, may also be undertaken. Further preferred chemical modifications are those of one or more of the chemical groups —COOH, —OH, =NH, —NH$_2$, —SH to —COOR, —OR, —NHR, —NR2, —NHR, —NR, —SR; in which:

R is —CH=CH—R2, —C≡C—R2, —C(R2)=CH$_2$, —C(R2)=C(R3), —CH=NR2, —C(R2)=N—R3, a 4-7 C ring system with or without substitution, a 4-7 nitrogen heterocycle with or without substitution, or a $C_2$ to $C_8$ chain with 1 to 5 double or triple bonds with substitutions chosen from R1, R2, or R3, wherein R1 is H, —R, —NO$_2$, —CN, halide substituent, —N$_3$, —C1-8 alkyl, —(CH$_2$)NCO$_2$R2, —C2-8 alkenyl-CO$_2$R2, —O(CH$_2$)NCO$_2$R2, —C(O)NR2R3, —P(O)(OR2)$_2$, alkyl-substituted tetrazol-5-yl, —(CH$_2$)n-O—(CH$_2$)n-aryl, —NR2R3, —(CH$_2$)n-OR2, —(CH$_2$)n-SR2, —N(R2)C(O)R3, —S(O$_2$)NR2R3, —N(R2)S(O)$_2$)R3, —(CHR2)n-NR2R3, —C(O)R3, (CH$_2$)n-N(R3)C(O)R3, —N(R2)CR2R3, substituted or unsubstituted (CH$_2$)n-cycloalkyl, substituted or unsubstituted (CH$_2$)N-phenyl, or -cycle; wherein n is a number greater than 1;

R2 is H, halide substituent, alkyl, haloalkyl, —(CH$_2$)N-phenyl, —(CH$_2$)1-3-biphenyl, —(CH$_2$)1-4-Ph-N(SO$_2$—C1-2-alkyl)$_2$, —CO(CHR1)n-OR1, —(CHR1)n-heterocycle, —(CHR1)n-NH—CO—R1, —(CHR1)n-NH—SO$_2$R1, —(CHR1)n-Ph-N(SO$_2$—C1-2-alkyl)$_2$, —(CHR1)n-C(O)(CHR1)-NHR1, —(CHR1)n-C(S)(CHR1)-NHR1, —(CH$_2$)n-O—(CH$_2$)nCH$_3$, —CF$_3$, —C$_2$-C$_5$ acyl, —(CHR1)nOH, —(CHR1)nCO$_2$R1, —(CHR1)n-O-alkyl, —(CHR1)n-O—(CH$_2$)n-O-alkyl, —(CHR1)n-S-alkyl, —(CHR1)n-S(O)-alkyl, —(CHR1)n-S(O)$_2$)-alkyl, —(CHR1)n-S(O$_2$)—NHR3, —(CHR3)n-N$_3$, —(CHR3)nNHR4, a $C_2$ to $C_8$ chain alkene chain with 1 to 5 double bonds, a $C_2$ to $C_8$ chain alkyne chain with 1 to 5 triple bonds, substituted or unsubstituted —(CHR3)n heterocycle, substituted or unsubstituted saturated or unsaturated —(CHR3)n cycloalkyl; wherein n is a number greater than 1 and R1 and R3 may be identical or different;

R4 is H, —(CH$_2$)nOH, —C(O)OR5, —C(O)SR5, —(CH$_2$)n-C(O)NR6R7, —O—C(O)—O—R6, an amino acid or a peptide; wherein n is a number from 0 to 4;

R5 is H;

R6 is —C(R7)-(CH$_2$)n-O—C(O)—R8, —(CH$_2$)n-C(R7)-O—C(O)R8, —(CH$_2$)n-C(R7)-O—C(O)—O—R8, or —C(R7)-(CH$_2$)n-O—C(O)—O—R8; wherein n is a number from 0 to 4; and R7 and R8 are each H, alkyl, substituted alkyl, aryl, substituted aryl, alkenyl, substituted alkenyl, alkynyl, substituted alkynyl, heterocycle, substituted heterocycle, alkylaryl, substituted alkylaryl, cycloalkyl, substituted cycloalkyl, or CH$_2$CO$_2$-alkyl, wherein R7 and R8 may be identical or different.

According to the invention, it is additionally possible to use all possible combinations of the substances stated above as belonging to (i), (ii) or (iii) and/or the derivatives thereof.

A liquid washing or cleaning agent according to the invention may be used as such or after dilution with water for cleaning textiles and/or hard surfaces. Such a dilute solution may readily be produced by diluting a portion of the agent in a further quantity of water in specific ratios by weight of agent:water and optionally this dilution is shaken to ensure uniform distribution of the agent in the water. Possible weight or volume ratios of the dilution are from 1:0 agent:water to 1:10000 or 1:20000 agent:water, preferably from 1:10 to 1:2000 agent:water.

All liquid or flowable presentations here may serve as liquid washing or cleaning agents. "Flowable" for the purposes of the present application means agents which can be poured and can exhibit viscosities of up to several tens of thousand mPa·s. Viscosity can be measured with conventional standard methods (e.g., Brookfield LVT-II viscosimeter at 20 rpm and 20° C., spindle 3) and is preferably in a range of from 5 to 10000 mPa·s. Preferred agents have viscosities of 10 to 8000 mPa·s, with values of 120 to 3000 mPa·s being particularly preferred. A liquid washing or cleaning agent for the purposes of the present invention may therefore also take the form of a gel or a paste, it may be present as a homogeneous solution or suspension, and, for example, be formulated as a sprayable or other conventional presentation. Washing agents include all conceivable types of washing agent, particularly washing agents for textiles, carpets or natural fibers. They may be provided for manual and/or machine use. Washing agents further include washing auxiliaries to achieve a further effect, which may be added to the actual washing agent for manual or machine washing of textiles. Cleaning agents include all agents, likewise arising in all the stated presentations, for cleaning and/or disinfecting hard surfaces, manual and automatic dishwashing agents, carpet cleaners, scouring agents, glass cleaners, WC rimblocks, etc. Finally, textile pre- and post-treatment agents include those agents with which an item of laundry is brought into contact before actual washing, for example, to partially dissolve stubborn soiling, as well as those which in a step downstream of the actual washing process impart to the washed item further desirable characteristics such as pleasant handle, absence of creases or low static charge. The latter agents include inter alia rinse conditioners. Disinfectants include hand disinfectants, surface disinfectants and instrument disinfectants, which may likewise occur in the stated presentations.

In a further preferred embodiment, the washing or cleaning agent has at least one further ingredient, particularly one chosen from surfactants, builders, peroxy compounds, bleach activators, alcohols, acids, graying inhibitors, optical brighteners, foam inhibitors, water-soluble salts, thickeners, volatile alkali and/or base hydrophilizing agents and combinations thereof.

Anionic, nonionic, zwitterionic and/or amphoteric surfactants can be used as surfactant(s). From an application standpoint, mixtures of anionic and nonionic surfactants are preferred. Total surfactant content of the liquid washing or cleaning agent liquid is preferably 60 wt. % or less, and particularly preferably 45 wt. % or less, based on total liquid washing or cleaning agent.

Suitable nonionic surfactants include alkoxylated fatty alcohols, alkoxylated fatty acid alkyl esters, fatty acid amides, alkoxylated fatty acid amides, polyhydroxyfatty acid amides, alkylphenol polyglycol ethers, amine oxides, alkyl polyglucosides and mixtures thereof.

Alkoxylated, advantageously ethoxylated, particularly primary alcohols with preferably 8 to 18 C atoms and on average 1 to 12 mol of ethylene oxide (EO) per mol of alcohol, in which the alcohol residue may be linear or preferably methyl-branched in position 2 or may contain linear and methyl-branched residues in the mixture, as are usually present in oxo alcohol residues, are preferably used as nonionic surfactants. In particular, however, alcohol ethoxylates with linear residues prepared from alcohols of natural origin with 12 to 18 C atoms, for example from coconut, palm, tallow fat or oleyl alcohol, and on average 2 to 8 EO per mol of alcohol are preferred. Preferred ethoxylated alcohols include, for example, $C_{12-14}$ alcohols with 3 EO, 4 EO or 7 EO, $C_{9-11}$ alcohols with 7 EO, $C_{13-15}$ alcohols with 3 EO, 5 EO, 7 EO or 8 EO, $C_{12-18}$ alcohols with 3 EO, 5 EO or 7 EO and mixtures of these, such as mixtures of $C_{12-14}$ alcohols with 3 EO and $C_{12-18}$ alcohols with 7 EO. The stated degrees of ethoxylation are statistical averages which, for a specific product, may be an integer or a fractional number. Preferred alcohol ethoxylates have a narrow homologue distribution (narrow range ethoxylates, NRE). In addition to these nonionic surfactants, fatty alcohols with more than 12 EO may also be used. Examples of these are tallow fatty alcohol with 14 EO, 25 EO, 30 EO or 40 EO. Nonionic surfactants containing EO and PO groups together in one molecule may also be used according to the invention. A mixture of a (more highly) branched ethoxylated fatty alcohol and an unbranched ethoxylated fatty alcohol, such as for example a mixture of a $C_{16-18}$ fatty alcohol with 7 EO and 2-propylheptanol with 7 EO is furthermore also suitable. Particularly preferably, the washing, cleaning or post-treatment agent or washing auxiliary contains a $C_{12-18}$ fatty alcohol with 7 EO or a $C_{13-15}$ oxo alcohol with 7 EO as nonionic surfactant.

The amount of nonionic surfactants in the washing or cleaning agent is preferably 3 to 40 wt. %, more preferably 5 to 30 wt. % and in particular 7 to 20 wt. %, based on total washing or cleaning agent.

In addition to nonionic surfactants, the washing or cleaning agent may also contain anionic surfactants. Sulfonates, sulfates, soaps, alkyl phosphates, anionic silicone surfactants and mixtures thereof are preferably used as the anionic surfactant.

Sulfonate surfactants which may preferably be considered are $C_{9-13}$ alkylbenzene sulfonates, olefin sulfonates, i.e. mixtures of alkene and hydroxyalkane sulfonates and disulfonates, as obtained, for example, from $C_{12-18}$ monoolefins with a terminal or internal double bond by sulfonation with gaseous sulfur trioxide and subsequent alkaline or acidic hydrolysis of the sulfonation products. $C_{12-18}$ alkane sulfonates and the esters of α-sulfofatty acids (ester sulfonates), for example, α-sulfonated methyl esters of hydrogenated coconut, palm kernel or tallow fatty acids, are also suitable.

Preferred alk(en)yl sulfates are the alkali metal, particularly sodium salts of sulfuric acid semi-esters of $C_{12}$-$C_{18}$ fatty alcohols, for example, prepared from coconut fatty alcohol, tallow fatty alcohol, lauryl, myristyl, cetyl or stearyl alcohol or $C_{10}$-$C_{20}$ oxo alcohols and those semi-esters of secondary alcohols of these chain lengths. $C_{12}$-$C_{16}$ Alkyl sulfates and $C_{12}$-$C_{15}$ alkyl sulfates and $C_{14}$-$C_{15}$ alkyl sulfates are preferred because of their washing characteristics. 2,3-Alkyl sulfates are also suitable anionic surfactants.

Sulfuric acid monoesters of straight-chain or branched $C_{7-21}$ alcohols ethoxylated with 1 to 6 mol of ethylene oxide are also suitable, such as 2-methyl-branched $C_{9-11}$ alcohols with on average 3.5 mol of ethylene oxide (EO) or $C_{12-18}$ fatty alcohols with 1 to 4 EO.

Soaps are also preferred anionic surfactants. Saturated and unsaturated fatty acid soaps are particularly suitable, such as the salts of lauric acid, myristic acid, palmitic acid, stearic acid, (hydrogenated) erucic acid and behenic acid and in particular soap mixtures derived from natural fatty acids, for example, coconut, palm kernel, olive oil or tallow fatty acids.

Anionic surfactants including soaps may be present in the form of the sodium, potassium, magnesium or ammonium salts thereof. Anionic surfactants are preferably present in the form of the sodium salts thereof. Further preferred counterions for the anionic surfactants are the protonated forms of choline, triethylamine or methylethylamine.

Anionic surfactant content of a washing or cleaning agent may amount to 1 to 40 wt. %, preferably 5 to 30 wt. % and very particularly preferably 10 to 25 wt. %, based on total washing or cleaning agent.

Possible builders which may be present in the washing or cleaning agent include silicates, aluminum silicates (particularly zeolites), carbonates, salts of organic di- and polycarboxylic acids and mixtures of these substances.

Organic builders which may be present in the washing or cleaning agent are, for example, polycarboxylic acids, which are usable in the form of the sodium salts thereof, polycarboxylic acids being taken to mean those carboxylic acids which bear more than one acid function. These are, for example, citric acid, adipic acid, succinic acid, glutaric acid, malic acid, tartaric acid, maleic acid, fumaric acid, saccharic acids, aminocarboxylic acids, nitrilotriacetic acid (NTA), methylglycinediacetic acid (MGDA) and the derivatives and mixtures thereof. Preferred salts are the salts of polycarboxylic acids such as citric acid, adipic acid, succinic acid, glutaric acid, tartaric acid, saccharic acids and mixtures of these.

Polymeric polycarboxylates are furthermore suitable as builders. These include the alkali metal salts of polyacrylic acid or of polymethacrylic acid, for example, those with a relative molecular mass of 600 to 750,000 g/mol.

Suitable polymers include polyacrylates, which preferably have a molecular mass of 1000 to 15,000 g/mol. Due to their superior solubility, short-chain polyacrylates from this group may in turn be preferred, these having molar masses of from 1000 to 10,000 g/mol, and particularly preferably from 1000 to 5000 g/mol.

Also suitable are copolymeric polycarboxylates, particularly those of acrylic acid with methacrylic acid and acrylic acid or methacrylic acid with maleic acid. In order to improve water solubility, the polymers may also contain allylsulfonic acids such as allyloxybenzenesulfonic acid and methallylsulfonic acid as a monomer.

Preferably, however, soluble builders, such as citric acid, or acrylic polymer with molar masses of 1000 to 5000 g/mol are preferably used in the liquid washing or cleaning agents.

Such organic builder substances may, if desired, be present in amounts of up to 40 wt. %, particularly up to 25 wt. % and preferably 1 wt. % to 8 wt. %. Quantities close to the stated upper limit are preferably used in pasty or liquid, particularly water-containing, agents.

Peroxy compounds suitable for use in agents according to the invention include organic peracids or peracid salts of organic acids such as phthalimidopercaproic acid, perbenzoic acid or salts of diperdodecanedioic acid, hydrogen peroxide and inorganic salts which release hydrogen peroxide under washing conditions, which latter include perborate, percarbonate, persilicate and/or persulfate such as caroate. If an agent contains peroxy compounds, these are preferably present in amounts of up to 50 wt. %, particularly 5 wt. % to 30 wt. %. It may be appropriate to add small quantities of known bleaching agent stabilizers such as phosphonates, borates or metaborates and metasilicates and magnesium salts such as magnesium sulfate.

Bleach activators which may be used are compounds which, under perhydrolysis conditions, yield aliphatic peroxycarboxylic acids with preferably 1 to 10 C atoms, particularly 2 to 4 C atoms, and/or optionally substituted perbenzoic acid. Suitable substances are those which bear O- and/or N-acyl groups having the stated number of C atoms and/or optionally substituted benzoyl groups. Preference is given to polyacylated alkylenediamines, particularly tetraacetylethylenediamine (TAED), acylated triazine derivatives, particularly 1,5-diacetyl-2,4-dioxohexahydro-1,3,5-triazine (DADHT), acylated glycolurils, particularly tetraacetylglycoluril (TAGU), N-acylimides, particularly N-nonanoyl succinimide (NOSI), acylated phenolsulfonates, particularly n-nonanoyl or isononanoyl oxybenzenesulfonate (n- or iso-NOBS), carboxylic anhydrides, particularly phthalic anhydride, acylated polyhydric alcohols, particularly triacetin, ethylene glycol diacetate, 2,5-diacetoxy-2,5-dihydrofuran and enol ester, as well as acetylated sorbitol and mannitol and/or the described mixtures thereof (SORMAN), acylated sugar derivatives, particularly pentaacetyl glucose (PAG), pentaacetyl fructose, tetraacetyl xylose and octaacetyl lactose and acetylated, optionally N-alkylated glucamine and gluconolactone, and/or N-acylated lactams, for example, N-benzoylcaprolactam. Hydrophilically substituted acyl acetals and acyl lactams are likewise preferably used. Combinations of conventional bleach activators may also be used. Such bleach activators may be present, particularly in the presence of the above-stated hydrogen peroxide-releasing bleaching agents, in a conventional quantity range, preferably in amounts of 0.5 wt. % to 10 wt. %, particularly 1 wt. % to 8 wt. %, based on total agent, but are preferably entirely absent when percarboxylic acid is used as the sole bleaching agent.

In addition to or instead of conventional bleach activators, sulfone imines and/or bleach-boosting transition metal salts or transition metal complexes may also be present as "bleach catalysts".

Washing or cleaning agents according to the invention are liquid and preferably contain water as the main solvent. In addition, nonaqueous solvents can be added to the washing or cleaning agent. Suitable nonaqueous solvents include mono- or polyhydric alcohols, alkanolamines or glycol ethers, insofar as they are water-miscible in the stated concentration range. The solvents are preferably chosen from ethanol, n-propanol, i-propanol, butanols, glycol, propanediol, butanediol, glycerol, diglycol, diethylene glycol propyl ether, diethylene glycol monobutyl ether, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl ether, propylene glycol ethyl ether, propylene glycol propyl ether, dipropylene glycol monomethyl ether, dipropylene glycol monoethyl ether, diisopropylene glycol monomethyl ether, diisopropylene glycol monoethyl ether, methoxytriglycol, ethoxytriglycol, butoxytriglycol, 1-butoxyethoxy-2-propanol, 3-methyl-3-methoxybutanol, propylene glycol-t-butylether, di-n-octyl ether and mixtures of these solvents. It is, however, preferred for the washing or cleaning agents to contain a polyol as nonaqueous solvent. Polyols include glycerol, 1,2-propanediol, 1,3-propanediol, ethylene glycol, diethylene glycol and/or dipropylene glycol. Particularly preferably, the washing or cleaning agent contains a mixture of a polyol and a monohydric alcohol. Nonaqueous solvents may be used in the washing or cleaning agents in amounts of 0.5 to 15 wt. %, but preferably 12 wt. % or less.

In order to establish a desired pH value which is not automatically obtained by mixing the remaining components, the agents may contain acids which are compatible with the system and are environmentally compatible, particularly citric acid, acetic acid, tartaric acid, malic acid, lactic acid, glycolic acid, succinic acid, glutaric acid and/or adipic acid, as well as mineral acids, particularly sulfuric acid, or bases, particularly ammonium or alkali metal hydroxides. Such pH regulators are present in the agents in amounts of preferably no more than 20 wt. %, particularly 1.2 wt. % to 17 wt. %.

Graying inhibitors have the task of keeping dirt which has been dissolved away from the textile fiber suspended in the liquor. Water-soluble colloids of a mainly organic nature are suitable for this purpose, for example, starch, size, gelatin, salts of ether carboxylic acids or ether sulfonic acids of starch or cellulose or salts of acidic sulfuric acid esters of cellulose or starch. Water-soluble polyamides containing acidic groups are also suitable for this purpose. Derivatives of starch other than those stated above, for example aldehyde starches, may further be used. Cellulose ethers, such as carboxymethylcellulose (Na salt), methylcellulose, hydroxyalkylcellulose and mixed ethers, such as methyl hydroxyethylcellulose, methylhydroxypropylcellulose, methylcarboxymethylcellulose and mixtures thereof, are preferably used, for example, in amounts of 0.1 to 5 wt. %, relative to the agent.

Textile washing agents can, for example, contain derivatives of diaminostilbene disulfonic acid or the alkali metal salts thereof as optical brighteners, although they preferably contain no optical brighteners for use as a color washing product. Suitable compounds include salts of 4,4'-bis(2-anilino-4-morpholino-1,3,5-triazinyl-6-amino)stilbene 2,2'-disulfonic acid or compounds of similar structure which, instead of the morpholino group, bear a diethanolamino group, a methylamino group, an anilino group or a 2-methoxyethylamino group. Brighteners of the substituted diphenylstyryl type may furthermore be present, for example, the alkali metal salts of 4,4'-bis(2-sulfostyryl)-diphenyl, 4,4'-bis(4-chloro-3-sulfostyryl)-diphenyl, or 4-(4-chlorostyryl)-4'-(2-sulfostyryl)-diphenyl. Mixtures of the above-stated optical brighteners can also be used.

Especially in machine washing methods, it may be advantageous to add foam inhibitors to the agents. Suitable foam inhibitors include soaps of natural or synthetic origin having an elevated proportion of $C_{18}$-$C_{24}$ fatty acids. Suitable non-surfactant foam inhibitors are, for example, organopolysiloxanes and mixtures thereof with microfine, optionally silanized silica as well as paraffins, waxes, microcrystalline waxes and mixtures thereof with silanized silica or bis-fatty acid alkylenediamides. Mixtures of different foam inhibitors are also advantageously used, for example, mixtures of silicones, paraffins or waxes. The foam inhibitors, particularly foam inhibitors containing silicone and/or paraffin, are preferably bound to a granular carrier substance which is soluble or dispersible in water. Mixtures of paraffins and bistearylethylenediamide are particularly preferred here.

An agent according to the invention may furthermore contain one or more water-soluble salts, which serve for example to adjust viscosity. The salts may be inorganic and/or organic. Inorganic salts which may be used are preferably chosen from colorless water-soluble halides, sulfates, sulfites, carbonates, hydrogencarbonates, nitrates, nitrites, phosphates and/or oxides of alkali metals, alkaline earth metals, of aluminum and/or the transition metals; ammonium salts may furthermore be used. Halides and sulfates of alkali metals are particularly preferred; the inorganic salt is therefore preferably chosen from sodium chloride, potassium chloride, sodium sulfate, potassium sulfate and mixtures thereof. Examples of organic salts which may be used are colorless water-soluble alkali metal, alkaline earth metal, ammonium, aluminum and/or transition metal salts of the carboxylic acids. The salts are preferably chosen from formate, acetate, propionate, citrate, malate, tartrate, succinate, malonate, oxalate, lactate and mixtures thereof.

For thickening purposes, an agent according to the invention may contain one or more thickeners. The thickener is preferably chosen from xanthan, guar, carrageenan, agar-agar, gellan, pectin, locust bean flour and mixtures thereof. These compounds are effective thickeners even in the presence of inorganic salts. In a particularly preferred embodiment, the washing or cleaning agent contains xanthan as thickener, since xanthan thickens effectively even in the presence of elevated salt concentrations and prevents macroscopic separation of the continuous phase. In addition, the thickener stabilizes the continuous, low-surfactant phase and prevents macroscopic phase separation.

Alternatively or in addition, (meth)acrylic acid (co)polymers may also be used as thickeners. Suitable acrylic and methacrylic (co)polymers include, for example, high molecular weight homopolymers, crosslinked with a polyalkenyl polyether, particularly an allyl ether of sucrose, pentaerythritol or propylene, of acrylic acid (INCI name according to the "International Dictionary of Cosmetic Ingredients" of "The Cosmetic, Toiletry, and Fragrance Association (CTFA)": Carbomer), also known as carboxyvinyl polymers. Such polyacrylic acids are obtainable inter alia under the trade names Polygel® and Carbopol®. The following acrylic acid copolymers are, for example, also suitable: (i) copolymers of two or more monomers from the group comprising acrylic acid, methacrylic acid and the simple esters thereof, preferably formed with $C_{1-4}$ alkanols (INCI Acrylates Copolymer), obtainable, for example, under the trade names Aculyn®, Acusol® or Tego® Polymer; (ii) crosslinked high molecular weight acrylic acid copolymers, which include copolymers crosslinked with an allyl ether of sucrose or of pentaerythritol, of $C_{10-30}$ alkyl acrylates with one or more monomers from the group comprising acrylic acid, methacrylic acid and the simple esters thereof, preferably formed with $C_{1-4}$ alkanols (INCI Acrylates/$C_{10-30}$ Alkyl Acrylate Crosspolymer) and which are obtainable, for example, under the trade name Carbopol®. Further suitable polymers are (meth)acrylic acid (co)polymers of the Sokalan® type.

It may be preferable for the washing or cleaning agent according to the invention to contain a (meth)acrylic acid (co)polymer in combination with a further thickener, preferably xanthan. The washing or cleaning agent can contain 0.05 to 1.5 wt. %, and preferably 0.1 to 1 wt. % of thickener, based on total washing or cleaning agent. The amount of thickener used is dependent on the type of thickener and the desired degree of thickening.

A corresponding agent may furthermore contain volatile alkali. Ammonia and/or alkanolamines, having up to 9 C atoms per molecule, are used as such.

Among alkanolamines, ethanolamines are preferred and, among these, monoethanolamine is in turn preferred. The content of ammonia and/or alkanolamine preferably amounts to 0.01 to 2 wt. %; ammonia is particularly preferably used. Small quantities of bases may additionally also be included. Preferred bases originate from the group of alkali metal and alkaline earth metal hydroxides and carbonates, particularly alkali metal hydroxides, among which potassium hydroxide and above all sodium hydroxide are particularly preferred.

A corresponding agent may also contain a hydrophilizing agent. For the purposes of the present invention, this means agents for hydrophilizing surfaces. Colloidal silica sols, in which the silicon dioxide is present preferably in nanoparticulate form, are suitable for hydrophilization. Colloidal nanoparticulate silica sols for the purposes of the present invention are stable dispersions of amorphous particulate silicon dioxide $SiO_2$ with particle sizes in the range from 1 to 100 nm. Particle sizes here are in the range from 3 to 50 nm, particularly preferably from 4 to 40 nm. One example of a silica sol suitable for use for the purposes of the present invention is the silica sol with a particle size of 9 nm obtainable under the trade name Bindzil® 30/360 from Akzo. Further suitable silica sols are Bindzil® 15/500, 30/220, 40/200 (Akzo), Nyacol® 215, 830, 1430, 2034DI and Nyacol® DP5820, DP5480, DP5540 etc. (Nyacol Products), Levasil® 100/30, 100F/30, 100S/30, 200/30, 200F/30, 300F/30, VP 4038, VP 4055 (H.C. Starck/Bayer) or indeed CAB-O-SPERSE® PG 001, PG 002 (aqueous dispersions of CAB-O-SIL®, Cabot), Quartron PL-1, PL-3 (FusoChemical Co.), Köstrosol 0830, 1030, 1430 (Chemiewerk Bad Köstritz). Silica sols used may also be surface-modified silica which has been treated with sodium aluminate (alumina-modified silica).

In addition, certain polymers may also be used for hydrophilizing surfaces. Suitable hydrophilizing polymers include amphoteric polymers, for example, copolymers prepared from acrylic or methacrylic acid and MAPTAC, DADMAC or another polymerizable quaternary ammonium compound. Copolymers with AMPS (2-acrylamido-2-methylpropanesulfonic acid) may also be used. Polyethersiloxanes, namely copolymers of polymethylsiloxanes with ethylene oxide or propylene oxide segments, are further suitable polymers. Acrylic polymers, maleic acid copolymers and polyurethanes with PEG (polyethylene glycol) units are likewise usable. Suitable polymers are commercially obtainable, for example, under the trade names Mirapol Surf-S100, 110, 200, 210, 400, 410, A 300, A 400 (Rhodia), Tegopren 5843 (Goldschmidt), Sokalan CP 9 (BASF) or Polyquart Ampho 149 (Cognis).

Ingredients chosen for the agent as well as the conditions under which it is applied according to the invention, such as temperature, pH value, ionic strength, redox ratios or mechanical influences, are conventionally optimized for the respective field of application.

Liquid or pasty agents according to the invention in the form of solutions containing conventional solvents are generally produced by simply mixing the ingredients, which may be introduced into an automatic mixer as an undissolved material or as a solution.

Washing or cleaning agents according to the invention may contain only a protease as described. Alternatively, they may also contain further hydrolytic or other enzymes in a concentration convenient for the efficacy of the agent. The invention thus further provides agents which additionally comprise one or more further enzymes, wherein all enzymes in general established for this purpose in the prior art may be used. Further enzymes which may preferably be used are enzymes which may exhibit a catalytic activity in the agent according to the invention, particularly a protease, amylase, cellulase, hemicellulase, mannanase, tannase, xylanase, xanthanase, β-glucosidase, carrageenase, perhydrolase, oxidase, oxidoreductase or a lipase, preferably together with mixtures thereof. These enzymes are generally of natural origin; starting from the natural molecules, improved variants are available for use in washing and cleaning agents, said variants accordingly preferably being used.

Agents according to the invention preferably contain enzymes in total quantities of $1 \times 10^{-8}$ to 5 wt. %, relative to active protein. The enzymes are preferably present in agents according to the invention in amounts from 0.001 to 5 wt. %, more preferably from 0.01 to 5 wt. %, still more preferably from 0.05 to 4 wt. % and particularly preferably from 0.075 to 3.5 wt. %, each enzyme which is included possibly being present in the stated quantity ratios. The enzymes may be adsorbed onto carrier substances and/or be embedded in encapsulating substances in order to protect them from premature inactivation Protein concentration can be determined using known methods, for example, the BCA method (bicinchoninic acid; 2,2'-biquinolyl-4,4'-dicarboxylic acid) or the biuret method (A. G. Gornau, C. S. Bardawill and M. M. David, J. Biol. Chem., 177, (1948) pp. 751-766).

Particularly preferably, the enzymes exhibit synergistic effects with regard to their action relative to specific soiling or stains, i.e. the enzymes contained in the agent composition assist one another's cleaning performance. Very particularly preferably, such a synergistic action is present between the protease according to the invention and a further enzyme of an agent according to the invention, including in particular between the stated protease and an amylase and/or a mannanase and/or a lipase. Synergistic effects may occur not only between different enzymes, but also between one or more enzymes and further ingredients of the agent according to the invention.

Among proteases, those of the subtilisin type are preferred. Examples of these are subtilisins BPN' and Carlsberg, protease PB92, subtilisins 147 and 309, alkaline protease from *Bacillus lentus*, subtilisin DY and the enzymes thermitase, proteinase K and proteases TW3 and TW7, which are classed among subtilases but no longer among the subtilisins as more narrowly defined. Subtilisin Carlsberg is obtainable in a further developed form under the trade name Alcalase® from Novozymes A/S, Bagsvaerd, Denmark. Subtilisins 147 and 309 are distributed under the trade name Esperase®, or Savinase® by Novozymes. The protease variants sold under the name BLAND are derived from the protease from *Bacillus lentus* DSM 5483. Further usable proteases include enzymes obtainable under the trade names Durazym®, Relase®, Everlase®, Nafizym, Natalase®, Kannase® and Ovozymes® from Novozymes, those obtainable under the trade names Purafect®, Purafect® OxP, Purafect® Prime, Excellase® and Properase® from Genencor, those obtainable under the trade name Protosol® from Advanced Biochemicals Ltd., Thane, India, those obtainable under the trade name Wuxi® from Wuxi Snyder Bioproducts Ltd., China, those obtainable under the trade names Proleather® and Protease P® from Amano Pharmaceuticals Ltd., Nagoya, Japan, and those obtainable under the name Proteinase K-16 from Kao Corp., Tokyo, Japan. The proteases from *Bacillus gibsonii* and *Bacillus pumilus* are also particularly preferably used, these being disclosed in International Patent Applications WO2008/086916 and WO2007/131656.

Examples of amylases formulatable according to the invention are α-amylases from *Bacillus licheniformis, B. amyloliquefaciens* or *B. stearothermophilus* and the further developments thereof enhanced for use in washing and cleaning agents. The enzyme from *B. licheniformis* is obtainable from Novozymes under the name Termamyl® and from Genencor under the name Purastar® ST. Further developed products of this α-amylase are obtainable from Novozymes under the trade name Duramyl® and Termamyl® ultra, from Genencor under the name Purastar® OxAm and from Daiwa Seiko Inc., Tokyo, Japan, as Keistase®. The α-amylase from *B. amyloliquefaciens* is distributed by Novozymes under the name BAN®, and variants derived from the α-amylase from *B. stearothermophilus* are distributed under names BSG® and Novamyl®, likewise by Novozymes.

Particular note should furthermore be taken for this purpose of the α-amylase from *Bacillus* sp. A 7-7 (DSM 12368) and the cyclodextrin glucanotransferase (CGTase) from *B. agaradherens* (DSM 9948). In addition, those amylolytic enzymes may be used which belong to the sequence space of α-amylases, which is defined in International Patent Application WO 03/002711 (A2), and those which are described in Application WO 03/054177 A2. Fusion products of the stated molecules may likewise be used.

Furthermore, the further developments of α-amylase from *Aspergillus niger* and *A. oryzae* obtainable under the trade name Fungamyl® from Novozymes are also suitable. Further commercial products which may be used include Amylase-LT® and Stainzyme® or Stainzyme® ultra or Stainzyme® plus, the latter likewise from Novozymes. Variants of these enzymes obtainable by point mutations may also be used according to the invention.

Examples of lipases or cutinases formulatable according to the invention, which are included in particular not only because of their triglyceride-cleaving activity but also to produce peracids in situ from suitable precursors, are lipases obtainable or further developed originally from *Humicola lanuginosa* (*Thermomyces lanuginosus*), particularly those with the amino acid substitution D96L. They are distributed, for example, by Novozymes under the trade name Lipolase®, Lipolase® Ultra, LipoPrime®, Lipozyme® and Lipex®. Furthermore, the cutinases originally isolated from, for example, *Fusarium solani pisi* and *Humicola insolens* are also usable. Lipases which are likewise usable are obtainable from Amano under the names Lipase® CE, Lipase® P, Lipase® B, or Lipase® CES, Lipase® AKG, *Bacillus* sp. Lipase®, Lipase® AP, Lipase® M-AP and Lipase® AML. Lipases or cutinases from Genencor which can, for example, be used are those whose initial enzymes were originally isolated from *Pseudomonas mendocina* and *Fusarium solanii*. Further important commercial products which may be mentioned are the preparations M1 Lipase® and Lipomax®, originally distributed by Gist-Brocades, and the enzymes distributed by Meito Sangyo KK, Japan, under the names Lipase® MY-30, Lipase® OF and Lipase® PL, as may be the product Lumafast® from Genencor.

Washing or cleaning agents may furthermore contain cellulases, depending on the intended purpose as pure enzymes, as enzyme preparations or in the form of mixtures in which the individual components advantageously complement each other with regard to their various performance characteristics. These performance characteristics include contributions to the primary or secondary washing performance of the agent (antiredeposition action or graying inhibition), to finishing (fabric action) and even to the provision of a "stone washed" effect.

One usable fungal cellulase preparation with an elevated endoglucanase (EG) content or further developments thereof are offered for sale by Novozymes under the trade name Celluzyme®. The products Endolase® and Carezyme® likewise obtainable from Novozymes are based on the 50 kD EG or the 43 kD EG from *H. insolens* DSM 1800. Further possible commercial products from this company are Cellusoft®, Renozyme® and Celluclean®. The 20 kD EG cellulase from Melanocarpus, which is obtainable from AB Enzymes, Finland, under the trade names Ecostone® and Biotouch® may also be used. Further commercial products from AB Enzymes are Econase® and Ecopulp®. Further suitable cellulases are obtainable from *Bacillus* sp. CBS 670.93 and CBS 669.93, the one from *Bacillus* sp. CBS 670.93 being obtainable from Genencor under the trade name Puradax®. Further commercial products from Genencor are "Genencor detergent cellulase L" and IndiAge® Neutra.

Further enzymes covered by the term hemicellulases can also be used to remove particularly problematic soiling. These include mannanases, xanthan lyases, pectin lyases (=pectinases), pectin esterases, pectate lyases, xyloglucanases (=xylanases), pullulanases and β-glucanases. Mannanases suitable in this respect are obtainable, for example, under the names Gamanase® and Pektinex® AR from Novozymes, under the name Rohapec® B1L from AB Enzymes and under the name Pyrolase® from Diversa Corp., San Diego, Calif., USA. The β-glucanase isolated from *Bacillus subtilis* is obtainable under the name Cereflo® from Novozymes.

Hemicellulases particularly preferred according to the invention are mannanases, distributed, for example, under the trade names Mannaway® by Novozymes or Purabrite® by Genencor.

To increase bleaching action, agents according to the invention may also contain oxidoreductases, for example, oxidases, oxygenases, catalases, (which at low $H_2O_2$ concentrations react as peroxidase), peroxidases such as halo-, chloro-, bromo-, lignin, glucose or manganese peroxidases, dioxygenases or laccases (phenol oxidases, polyphenol oxidases). Suitable commercial products which may be mentioned are Denilite® 1 and 2 from Novozymes. For systems which may advantageously be used for enzymatic perhydrolysis, reference is made, for example, to applications WO 98/45398 A1, WO 2005/056782 A2 and WO 2004/058961 A1. A combined enzymatic bleaching system comprising an oxidase and a perhydrolase is described in application WO 2005/124012. Compounds, preferably organic compounds, particularly preferably aromatic compounds which interact with the enzymes, are advantageously also added in order to enhance the activity of the oxidoreductases in question (enhancers) or, in the event of a major difference in redox potential between the oxidizing enzymes and the soiling, to ensure electron flow (mediators).

Enzymes used according to the invention either originally originate from microorganisms, for example, of the genera *Bacillus, Streptomyces, Humicola,* or *Pseudomonas*, and/or are produced by suitable microorganisms using per se known biotechnological methods, for instance, by transgenic expression hosts from the genera *Bacillus* or by filamentous fungi. The enzymes in question are favorably purified by per se established methods, for example, by precipitation, sedimentation, concentration, filtration of the liquid phases, microfiltration, ultrafiltration, chemical action, deodorization or suitable combinations of these steps. The enzymes may additionally be formulated together with accompanying substances, for instance, from fermentation, or with stabilizers.

The invention also independently provides the use of a washing or cleaning agent according to the invention for removing soiling, particularly protease-sensitive soiling, from textiles or hard surfaces (i.e., for cleaning textiles or hard surfaces).

This is because agents according to the invention may, in particular due to the combination of protease and phosphonate contained therein, advantageously be used to remove corresponding soil from textiles or from hard surfaces. Embodiments of this aspect of the invention include hand washing, manual removal of stains from textiles or hard surfaces or use in connection with a machine method.

All factors, aspects and embodiments which have been described for washing or cleaning agents according to the invention are also applicable to this aspect of the invention. Express reference is therefore made at this point to the disclosure at corresponding points, it being pointed out that this disclosure also applies to the above use according to the invention.

The invention also further provides for methods for cleaning textiles or hard surfaces wherein a washing or cleaning agent according to the invention is used in at least one of the method steps. The method for cleaning textiles or hard surfaces is accordingly characterized in that in at least one method step a washing or cleaning agent according to the invention is used.

These include both manual and machine methods, with machine methods being preferred due to their being more precisely controllable, for example, in terms of the quantities used and exposure times.

Methods for cleaning textiles are in general distinguished in that in two or more method steps various substances with a cleaning action are applied onto the material to be cleaned and, after the exposure time, are washed off, or that the material to be cleaned is treated in some other manner with a washing agent or a solution or dilution of this agent. The same applies to methods for cleaning all materials other than textiles, in particular hard surfaces. Any conceivable washing or cleaning methods may be enhanced in at least one of the method steps by application of a washing or cleaning agent according to the invention and then constitute embodiments of the present invention.

All factors, aspects and embodiments which have been described for washing or cleaning agents according to the invention are also applicable to this aspect of the invention. Express reference is therefore made at this point to the disclosure at corresponding points, it being pointed out that this disclosure also applies to the above methods according to the invention.

In one preferred embodiment, the method is characterized in that the phosphonate is present in the washing liquor in a concentration of 0.00075 to 0.05 wt. %, and/or the protease is present in the washing liquor in a concentration of 0.0005 to 0.03 wt. %. Further preferred concentrations of the phosphonate present in the washing liquor are from 0.00075 to 0.01125 wt. %, from 0.001 to 0.035 wt. %, from 0.002 to 0.01125 wt. % or from 0.00375 to 0.0075 wt. %. Further preferred concentrations of the protease present in the washing liquor are from 0.00075 to 0.03 wt. % or from 0.00077 to 0.028 wt. %.

In a further preferred embodiment the method is performed at a temperature of from 10° C. to 60° C., 10° C. to 55° C., 10° C. to 50° C., 10° C. to 40° C. or 20° C. to 40° C.

Proteases used in agents according to the invention may advantageously be used, in accordance with the above explanations, in washing and cleaning agents according to the invention as well as in methods, particularly washing and cleaning methods. They may thus advantageously be used to provide proteolytic activity in corresponding agents.

The invention therefore further provides the use of a protease—

(a1) having an amino acid sequence which is at least 80% identical to the amino acid sequence stated in SEQ ID no. 1 and comprises in position 99 in the numbering according to SEQ ID NO. 1 the amino acid glutamic acid (E) or aspartic acid (D), or (a2) having an amino acid sequence which is at least 80% identical to the amino acid sequence stated in SEQ ID NO. 1 and comprises in position 99 in the numbering according to SEQ ID NO. 1 the amino acid asparagine (N) or glutamine (Q), or (a3) having an amino acid sequence which is at least 80% identical to the amino acid sequence stated in SEQ ID NO. 1 and comprises in position 99 in the numbering according to SEQ ID NO. 1 the amino acid alanine (A) or glycine (G) or serine (S), for providing proteolytic activity in a liquid washing or cleaning agent which furthermore comprises a phosphonate.

In a further embodiment of the invention this use is characterized in that the protease further comprises at least one of the following amino acids in the numbering according to SEQ ID NO. 1:

(a) threonine in position 3 (3T),
(b) isoleucine in position 4 (4I),
(c) alanine, threonine or arginine in position 61 (61A, 61T or 61R), (d) aspartic acid or glutamic acid in position 154 (154D or 154E),
(e) proline in position 188 (188P),
(f) methionine in position 193 (193M),
(g) isoleucine in position 199 (199I),
(h) aspartic acid, glutamic acid or glycine in position 211 (211D, 211E or 211G),
(i) combinations of amino acids (a) to (h).

The invention further provides for use of a protease chosen from—
a. protease comprising an amino acid sequence according to SEQ ID NO. 2, SEQ ID NO. 3, SEQ ID NO. 4, SEQ ID NO. 5, SEQ ID NO. 6, SEQ ID NO. 7 or SEQ ID NO. 8;
b. protease which, relative to SEQ ID NO. 2, SEQ ID NO. 3, SEQ ID NO. 4, SEQ ID NO. 5, SEQ ID NO. 6, SEQ ID NO. 7 or SEQ ID NO. 8, comprises an amino acid sequence modified in at least one position, the modification in the numbering according to SEQ ID NO. 1 being chosen from:
  i. threonine in position 3 (3T),
  ii. isoleucine in position 4 (4I),
  iii. alanine, threonine or arginine in position 61 (61A, 61T or 61R),
  iv. aspartic acid or glutamic acid in position 154 (154D or 154E),
  v. proline in position 188 (188P),
  vi. methionine in position 193 (193M),
  vii. isoleucine in position 199 (199I),
  viii. aspartic acid, glutamic acid or glycine in position 211 (211D, 211E or 211G),
  ix. combinations of amino acids (i) to (viii);
for providing proteolytic activity in a liquid washing or cleaning agent which furthermore comprises a phosphonate.

All factors, aspects and embodiments which have been described for washing or cleaning agents according to the invention are also applicable to the stated uses. Express reference is therefore made at this point to the disclosure at corresponding points, it being pointed out that this disclosure also applies to the above uses according to the invention.

EXAMPLES

All the molecular biological procedures follow standard methods as stated, for example, in the manual by Fritsch, Sambrook and Maniatis "Molecular cloning: a laboratory manual", Cold Spring Harbor Laboratory Press, New York, 1989, or comparable relevant works. Enzymes and kits were used as indicated by the respective manufacturer.

Example 1

Determination of Cleaning Performance of a Liquid Washing Agent According to the Invention For this example, textiles with standard soiling were used, which were obtained from EMPA Testmaterialien AG (St. Gallen, Switzerland), wfk Testgewebe GmbH (Brüggen-Bracht, Germany), or the Center For Test Materials (CFT, Vlaardingen, Netherlands). The following soiling and textiles were used:
A: grass on cotton: product no. 164 from Eidgenössische Material- and Prüfanstalt (EMPA) Testmaterialien AG, St. Gallen, Switzerland;
B: peanut oil-pigment/ink on polyester/cotton: product no. PC-10 from CFT (Center For Testmaterials) B.V. Vlaardingen, Netherlands;
C: whole egg/pigment (whole egg/soot) on cotton: product no. 10N from wfk Testgewebe GmbH; Brüggen-Bracht, Germany;
D: blood-milk/ink on cotton: product no. C-05 obtainable from CFT (Center For Test Materials) B.V. Vlaardingen, Netherlands Using this test material, various washing agents were investigated with regard to their cleaning performance. For this purpose, the formulations were washed for 60 minutes at temperatures of 40° C. or 20° C. The rate of addition was 7.4 grams of washing agent per liter of washing liquor. Washing was performed using mains water with a water hardness of approx. 16° dH (German hardness degrees). A washing agent base formulation as stated above in Table 1 was used as the washing agent.

This washing agent base formulation was combined at identical activity with the following proteases for the various series of tests (5 PU/ml of final concentration): protease including an amino acid sequence according to SEQ ID NO. 2 (formulation 1), performance-enhanced variant F49 of the protease from *Bacillus lentus* according to WO 95/23221 (formulation 2) and the protease disclosed in FIG. 2 or SEQ ID NO. 3 of International Patent Application Publication No. WO 03/057713 (formulation 3).

After washing the degree of whiteness of the washed textiles was measured. Measurement was performed using a Minolta CM508d spectrophotometer (illuminant D65, 10°). The apparatus was calibrated beforehand with the white standard supplied. The results obtained are the differential reflectance values between a washing process with a washing agent containing a protease and a parallel control washing operation carried out with a washing agent without protease. The results are set out in Table 2 below and permit a direct conclusion to be drawn as to the contribution of the enzyme contained in each case to the cleaning performance of the agent used.

TABLE 2

Washing results with a liquid washing agent at 40° C. and 20° C. respectively

| Soiling | Formulation 1 | | Formulation 2 | | Formulation 3 | |
| --- | --- | --- | --- | --- | --- | --- |
| | 40° C. | 20° C. | 40° C. | 20° C. | 40° C. | 20° C. |
| A | 1.4 | 1.3 | 1.4 | 0.4 | 1.0 | 0.7 |
| B | 5.2 | 4.9 | 4.0 | 2.9 | 4.9 | 4.2 |
| C | 3.0 | 3.5 | 4.9 | 2.3 | 2.1 | 2.4 |
| D | 16.7 | 12.6 | 13.6 | 11.4 | 15.4 | 11.1 |

It is clear that a washing agent according to the invention exhibits very good cleaning performance, and indeed better cleaning performance for most types of soiling, than do the washing agents of formulations 2 and 3.

Example 2

Determination of the Cleaning Performance of a Liquid Automatic Dishwashing Agent According to the Invention Vessels with hard, smooth surfaces were provided in standardized manner with the respective soiling and washed at 40° C. and at 50° C. using a conventional commercial domestic dishwashing machine. Each washing cycle was performed using 30 ml of a liquid or gel-form conventional commercial automatic dishwashing agent containing 2.4 wt. % phosphonate (HEDP). Washing was performed using mains water with a water hardness of approx. 21° dH (German hardness degrees). The protease used was Savinase ultra 16L (Novozymes, formulation 1) and a protease according to the invention comprising an amino acid sequence according to SEQ ID NO. 2 (formulation 2). The proteases were used in identical weights relative to enzyme protein (0.68 g Savinase ultra 16L or an identical weight of enzyme protein of the protease according to the invention per 30 ml of cleaning agent).

After washing, removal of the soiling was determined either gravimetrically (egg yolk) or visually (further soiling according to Table 3). The gravimetric determination was carried out by determining the difference between the weight of the soiled and the washed vessel (removed egg yolk) and relating this difference to the quantity of egg yolk originally applied according to the following formula: % cleaning performance=(mg removed egg yolk/mg applied egg yolk)×100. The visual determination was carried out by experienced assessors visually rating soil removal against a percentage scale. The results are set out in Table 3 below and permit a direct conclusion to be drawn as to the contribution of the enzyme contained in each case to the cleaning performance of the agent used.

TABLE 3

Cleaning performance of a liquid automatic dishwashing agent according to the invention at 40° C. and 50° C.

| Soiling | 40° C. | | 50° C. | |
|---|---|---|---|---|
| | Formulation 1 | Formulation 2 | Formulation 1 | Formulation 2 |
| Milk | 74 | 76 | 74 | 74 |
| Minced meat | 99 | 100 | 94 | 98 |
| Egg yolk | 37 | 47 | 47 | 65 |

It is clear that a liquid automatic dishwashing agent according to the invention exhibits very good cleaning performance which in particular against egg yolk soiling is indeed distinctly better than that of the dishwashing agent according to formulation 1.

Example 3

Determination of the Storage Stability of a Liquid Washing Agent According to the Invention Washing agents according to formulations 1 and 2 from Example 1 were tested for their storage stability. To this end, the washing agents were stored at a temperature of 30° C. for the period stated in each case and the respective residual proteolytic activity was determined on the basis of the liberation of the chromophore para-nitroaniline (PNA) from the substrate. The substrate is suc-L-Ala-L-Ala-L-Pro-L-Phe-p-nitroanilide (suc-AAPF-pNA). The protease cleaves the substrate and liberates pNA. Liberation of the PNA brings about an increase in absorbance at 410 nm, the time profile of which is a measure of enzymatic activity (cf. Del Mar et al., 1979). The measurement was carried out at a temperature of 25° C., at pH 8.6 and a wavelength of 410 nm. The measurement time was 5 min with a measurement interval of 20 s to 60 s. The residual activity values obtained are stated in Table 4 below.

TABLE 4

Determination of residual proteolytic activity after storage

| Washing agent according to | Start | Week 1 | Week 2 |
|---|---|---|---|
| Formulation 1 | 100% | 71% | 77% |
| Formulation 2 | 100% | 47% | 37% |

It is clear that a washing agent according to the invention exhibits distinctly improved storage stability in comparison with a washing agent according to formulation 2. The washing agent according to the invention exhibits proteolytic activity which is 151% higher after one week and 211% higher after two weeks.

We claim:

1. A liquid washing or cleaning agent comprising:
a protease having an amino acid sequence which is at least 80% identical to the amino acid sequence stated in SEQ ID NO. 1 and comprises in position 99 in the numbering according to SEQ ID NO. 1 the amino acid glutamic acid (E) and a phosphonate, wherein the phosphonate is diethylenetriaminepenta(methylenephosphonic acid) (DTPMP or DETPMP or DTPNT) or a combination thereof with one or more other phosphonates, wherein the washing or cleaning agent has improved cleaning performance.

2. The liquid washing or cleaning agent according to claim 1 wherein, based on the numbering according to SEQ ID NO. 1, the protease further comprises at least one of the following amino acids:
   (a) threonine in position 3 (3T),
   (b) isoleucine in position 4 (4I),
   (c) alanine, threonine or arginine in position 61 (61A, 61T or 61R),
   (d) aspartic acid or glutamic acid in position 154 (154D or 154E),
   (e) proline in position 188 (188P),
   (f) methionine in position 193 (193M),
   (g) isoleucine in position 199 (199I),
   (h) aspartic acid, glutamic acid or glycine in position 211 (211D, 211E or 211G),
   (i) combinations of amino acids (a) to (h).

3. A liquid washing or cleaning agent comprising:
   (a) a protease chosen from
      a. a protease comprising an amino acid sequence according to SEQ ID NO. 2 and
      b. a protease comprising an amino acid sequence differing from the amino acid sequence of SEQ ID NO. 2 by at least one modification chosen from:
         i. threonine in position 3 (3T),
         ii. isoleucine in position 4 (4I),
         iii. alanine, threonine or arginine in position 61 (61A, 61T or 61R),
         iv. aspartic acid or glutamic acid in position 154 (154D or 154E),
         v. praline in position 188 (188P),
         vi. methionine in position 193 (193M), vii. isoleucine in position 199 (199I),
viii. aspartic acid, glutamic acid or glycine in position 211 (211D, 211E or 211G), and
ix. combinations of amino acids (i) to (viii); and (b) a phosphonate, wherein the phosphonate is diethylenetriaminepenta(methylenephosphonic acid) (DTPMP or DETPMP or DTPNT) or a combination thereof with one or more other phosphonates.

4. The liquid washing or cleaning agent according to claim 1, wherein the phosphonate is present in an amount of 0.01 to 4 wt. %, and/or the protease is present in an amount of $1\times10^{-8}$ to 5 weight percent, based on active protein.

5. The liquid washing or cleaning agent according to claim 1 further comprising a component chosen from
(i) an anionic and/or polyanionic substance, and/or
(ii) a cationic and/or polycationic substance, and/or
(iii) a substance comprising hydroxyl and/or polyhydroxyl group(s).

6. The liquid washing or cleaning agent according to claim 1 further comprising one or more ingredients chosen from surfactants, builders, peroxy compounds, bleach activators, alcohols, acids, graying inhibitors, optical brighteners, foam inhibitors, water-soluble salts, thickeners, volatile alkali and/or base, hydrophilizing agents and combinations thereof.

7. The liquid washing or cleaning agent according to claim 1 further comprising at least one further enzyme.

8. The liquid washing or cleaning agent according to claim 7 wherein the at least one further enzyme is a protease, amylase, cellulase, hemicellulase, mannanase, tannase, xylanase, xanthanase, ß-glucosidase, carrageenase, perhydrolase, oxidase, oxidoreductase, lipase, or mixture thereof.

9. Method of removing protease-sensitive soiling from textiles or hard surfaces comprising applying a liquid washing or cleaning agent according to claim 1 onto the textiles or hard surfaces.

10. Method for cleaning textiles or hard surfaces comprising washing the textiles or cleansing the hard surface with the liquid washing or cleaning agent according to claim 1.

11. Method according to claim 10 wherein the phosphonate is present in a washing liquor in a concentration of 0.00075 to 0.05 wt. % and/or the protease is present in a washing liquor in a concentration of 0.0005 to 0.03 wt. %.

12. Method according to claim 10, wherein the washing is carried out at a temperature of from 10° C. to 60° C.

13. Method of improving cleaning performance of a liquid washing or cleaning agent comprising adding to the agent a protease and a phosphonate,
wherein the proteases has an amino acid sequence which is at least 80% identical to the amino acid sequence stated in SEQ ID NO. 1 and comprises in position 99 in the numbering according to SEQ ID NO. 1 the amino acid glutamic acid (E), and
wherein the phosphonate is diethylenetriaminepenta(methylenephosphonic acid) (DTPMP or DETPMP or DTPNT) or a combination thereof with one or more other phosphonates.

14. Method according to claim 13, wherein, in the numbering according to SEQ ID NO. 1, the protease further comprises at least one of the following amino acids:
(a) threonine in position 3 (3T),
(b) isoleucine in position 4 (4I)
(c) alanine, threonine or arginine in position 61 (61A, 61T or 61R),
(d) aspartic acid or glutamic acid in position 154 (154D or 154E),
(e) proline in position 188 (188P),
(f) methionine in position 193 (193M),
(g) isoleucine in position 199 (199I),
(h) aspartic acid, glutamic acid or glycine in position 211 (211D, 211E or 211G),
(i) combinations of amino acids (a) to (h).

* * * * *

SEQUENCE LISTING

<160> NUMBER OF SEQ ID NOS: 8

<210> SEQ ID NO 1
<211> LENGTH: 269
<212> TYPE: PRT
<213> ORGANISM: Bacillus lentus

<400> SEQUENCE: 1

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110
```

```
Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 2
<211> LENGTH: 269
<212> TYPE: PRT
<213> ORGANISM: Bacillus lentus

<400> SEQUENCE: 2

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
                35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Glu Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Ala
            210                 215                 220
```

```
Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265
```

<210> SEQ ID NO 3
<211> LENGTH: 269
<212> TYPE: PRT
<213> ORGANISM: Bacillus lentus

<400> SEQUENCE: 3

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Asp Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265
```

<210> SEQ ID NO 4
<211> LENGTH: 269
<212> TYPE: PRT
<213> ORGANISM: Bacillus lentus

<400> SEQUENCE: 4

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Asn Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 5
<211> LENGTH: 269
<212> TYPE: PRT
<213> ORGANISM: Bacillus lentus

<400> SEQUENCE: 5

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

```
Asp Gly Gln Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 6
<211> LENGTH: 269
<212> TYPE: PRT
<213> ORGANISM: Bacillus lentus

<400> SEQUENCE: 6

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Ala Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205
```

```
Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

<210> SEQ ID NO 7
<211> LENGTH: 269
<212> TYPE: PRT
<213> ORGANISM: Bacillus lentus

<400> SEQUENCE: 7

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Gly Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

<210> SEQ ID NO 8
<211> LENGTH: 269
<212> TYPE: PRT
<213

-continued

```
<400> SEQUENCE: 8

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Ser Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```